United States Patent
Alatraktchi et al.

(10) Patent No.: US 11,169,140 B2
(45) Date of Patent: Nov. 9, 2021

(54) ELECTROCHEMICAL DEVICE FOR DETECTION OF SELECTED QUORUM SENSING SIGNALS

(71) Applicant: Danmarks Tekniske Universitet, Kgs. Lyngby (DK)

(72) Inventors: Fatima Alzahra'a Alatraktchi, Greve (DK); Winnie Edith Svendsen, København S (DK)

(73) Assignee: Danmarks Tekniske Universitet, Kgs. Lyngby (DK)

( * ) Notice: Subject to any disclaimer, the term of this patent is extended or adjusted under 35 U.S.C. 154(b) by 88 days.

(21) Appl. No.: 16/093,300

(22) PCT Filed: Apr. 11, 2017

(86) PCT No.: PCT/EP2017/058614
§ 371 (c)(1),
(2) Date: Oct. 12, 2018

(87) PCT Pub. No.: WO2017/178455
PCT Pub. Date: Oct. 19, 2017

(65) Prior Publication Data
US 2019/0137478 A1    May 9, 2019

(30) Foreign Application Priority Data

Apr. 12, 2016 (EP) .................................. 16164840

(51) Int. Cl.
*G01N 27/327* (2006.01)
*G01N 33/487* (2006.01)
*G01N 27/27* (2006.01)
(Continued)

(52) U.S. Cl.
CPC ....... *G01N 33/48735* (2013.01); *G01N 27/27* (2013.01); *G01N 27/3277* (2013.01);
(Continued)

(58) Field of Classification Search
CPC ............... G01N 27/27; G01N 27/3277; G01N 27/3278; G01N 27/49
See application file for complete search history.

(56) References Cited

U.S. PATENT DOCUMENTS

| 8,641,876 B2 | 2/2014 | Chen |
| 8,691,065 B2 * | 4/2014 | Gau ..................... G01N 27/286 204/406 |
| 2007/0072174 A1 | 3/2007 | Sayler et al. |
| 2008/0249391 A1 | 10/2008 | Moxon et al. |

(Continued)

FOREIGN PATENT DOCUMENTS

| WO | 2013058879 A2 | 4/2013 |
| WO | 2014015333 A1 | 1/2014 |

(Continued)

OTHER PUBLICATIONS

Abu, E. A. et al.: "Cyclic voltammetric, fluorescence and biological analysis of purified aeruginosin A, a secreted red pigment of Pseudomonas aeruginosa PAO1, Microbiology", Aug. 2013;159(Pt 8):1736-47.

(Continued)

*Primary Examiner* — David W Berke-Schlessel
*Assistant Examiner* — Trent R Clarke
(74) *Attorney, Agent, or Firm* — Dinsmore & Shohl LLP

(57) ABSTRACT

An electrochemical device for diagnostic purposes, and particularly point-of-care diagnostic purposes, is capable of detecting quorum sensing molecules, such as AHL, within a biological sample with high precision. The device includes at least one reference electrode (RE), at least one counter electrode (CE), and two or more working electrodes (WEs). Each working electrode differs from the other working electrode(s) with respect to at least one of the following characteristics: surface area, size, material, and coating. The device also has a sample receiving area for receiving a (Continued)

biological sample, wherein the electrodes and the sample receiving area is fluidly connected, and a means for transferring the sample to the electrodes for measurement, and a means for displaying a result of the measurement.

21 Claims, 8 Drawing Sheets

(51) Int. Cl.
    *G01N 27/49*     (2006.01)
    *G01N 27/48*     (2006.01)

(52) U.S. Cl.
    CPC ......... *G01N 27/3278* (2013.01); *G01N 27/49* (2013.01); *G01N 27/48* (2013.01)

(56) References Cited

U.S. PATENT DOCUMENTS

| | | |
|---|---|---|
| 2009/0215079 A1 | 8/2009 | Ostermann et al. |
| 2019/0046984 A1* | 2/2019 | Kelley ............... G01N 1/40 |

FOREIGN PATENT DOCUMENTS

| | | | |
|---|---|---|---|
| WO | 2014165659 A2 | 10/2014 | |
| WO | 2015031798 A1 | 3/2015 | |
| WO | WO-2015031798 A1 * | 3/2015 | ........ B01L 3/502707 |

OTHER PUBLICATIONS

Alaktraktchi F. A. et al.: "Fast selective detection of pyocyanin using cyclic voltammetry", Sensors, vol. 16, No. 3, 408, Mar. 19, 2016.
Alaktraktchi, F. A. et al.: "Electrochemical sensing of biomarker for diagnostics of bacteria-specific infections", Nanomedicine, vol. 11, No. 16, Jul. 27, 2016.
Alaktraktchi, F. A. et al.: "Novel membrane-based electrochemical sensor for real-time bio-applications", Sensors, vol. 14, No. 11, Nov. 24, 2014.
Baldrich, E. et al. "Electrochemical detection of quorum sensing signaling molecules by dual signal confirmation at microelectrode arrays", Anal Chem. Mar. 15, 2011;83(6):2097-103.
Dimaki, M. et al.: "A compact microelectrode array chip with multiple measuring sites for electrochemical applications", Sensors, vol. 14, No. 6, May 28, 2014.
Oziat, J. et al.: "Electrochemistry provides a simple way to monitor Pseudomonas aeruginosa metabolites", 37th Annual International Conference of the IEEE Engineering in Medicine and Biology Society, IEEE, Aug. 25, 2015.
Webster, T. A. et al.: "Electrochemical detection of Pseudomonas aeruginosa in human fluid samples via pyocyanin", Biosens. Bioelectron., vol. 60, Apr. 29, 2014.
Zhou, L. et al.: "Analysis of Pseudomonas quinolone signal and other bacterial signalling molecules using capillaries coated with highly charged polyelectrolyte monolayers and boron doped diamond electrode", J Chromatogr A. Aug. 17, 2012;1251:169-75.
Zhou, L. et al.: "Detection of the Pseudomonas Quinolone Signal (PQS) by cyclic voltammetry and amperometry using a boron doped diamond electrode", Chem Commun (Camb). Oct. 7, 2011;47(37):10347-9.
Vergani, Marco; Multichannel Bipotentiostat Integrated With aMicro?uidic Platform for Electrochemical Real-Time Monitoring of Cell Cultures; EEE Transactions on Biomedical Circuits and Systems, vol. 6, No. 5, Oct. 2012.

* cited by examiner

ELECTROCHEMICAL DEVICE FOR DETECTION OF SELECTED QUORUM SENSING SIGNALS

CROSS-REFERENCE TO RELATED APPLICATIONS

This application is the U.S. national stage of PCT/EP2017/058614 filed Apr. 11, 2017, which claims priority of European Patent Application 16164840.7 filed Apr. 12, 2016 of which is hereby incorporated by reference in its entirety.

FIELD OF INVENTION

The present invention relates to an electrochemical device for detecting a presence and measuring a level of a quorum sensing molecule such as N-Acryl homoserine lactones (AHL) in a biological sample. The invention further relates to a method for detecting the presence of a selected quorum sensing molecule in a biological sample, and further to a method for measuring a level of a selected quorum sensing molecule in a biological sample. Particularly, the present disclosure relates to an electrochemical device and a method for detecting the presence of AHL in a biological sample.

BACKGROUND OF INVENTION

Chronic infections caused by antibiotic resistant bacteria are a growing concern for the world's health systems. The occurrence of chronic infections is increasing, and chronic infections are potentially lethal due to the risk of an infectious attack in the chronically infected individual.

Especially infections caused by Gram-negative bacteria constitute a major problem because these bacteria often develop antibiotic resistance and thereby have the opportunity to cause chronic infections. At the present time, it is not possible to discriminate between a superficial infection and a deep-seated chronic infection.

Quorum sensing signals are the signaling molecules that are involved in cell-to-cell communication and are responsible for the bacterial virulent behavior. This way, the quorum sensing signaling molecules can provide information about the type of bacterial infection and about its state of progression.

Quorum sensing molecules which may be indicators for bacterial virulent behavior include N-Acryl homoserine lactones (AHL), pyocyanin, 2-heptyl-3,4-dihydroxyquinoline (PQS), and 4-hydroxy-2-heptylquinoline (HHQ). Thus, the amount of e.g. AHL in a tissue or body fluids is an indication of the risk of an infection, as well as an indication of the risk of an infectious attack in a chronically infected individual.

The quorum sensing protein, e.g. AHL, is produced by bacteria. If the amount of AHL exceeds a certain level, the bacteria determine that the bacterial population is big enough to promote an infection.

Thus, monitoring and detection of the level of AHL before the bacterial population has reached the critical level, is a possibility for avoiding serious infections, as well as critical infectious attacks. This may be of particular relevance for patient groups with high risk of infections, such as cystic fibrosis patients.

Furthermore, monitoring of e.g. the AHL level may reduce the amount of antibiotics used due to earlier and more precise diagnosis, which will improve the efficiency of a treatment. Thus, monitoring of selected quorum sensing molecules may be used for optimizing antibiotic treatments, and further improve the life quality of the patients.

AHLs are conventionally detected by spectroscopic or chromatographic measurements on extracts. The conventional methods suffer from low sensitivity, as well as low efficiency as they are complex and time consuming to carry out. Furthermore, they are only applicable on pretreated extracts. Thus, measurement in vivo or real time experiments directly on the potentially infected patient, or infectious foci on the patient, cannot be carried out.

Alternatively, quorum sensing molecules may be detected by electrochemical measurements, e.g. using amperometric or potentiometric techniques.

US 2009/0215079 A1 [1] discloses an electrochemical sensor for monitoring quorum sensing molecules, which may comprise of an array of gold electrodes. The sensor is capable of simultaneous measuring quorum sensing activities of different microorganisms.

WO 2014/015333 A1 [2] discloses an electrochemical device for monitoring quorum sensing molecules, such as pyocyanin. The device may comprise an oxidizing and a reducing working electrode, for amplifying the signal, and the two working electrodes consist of gold.

Typically, a multiple of electro-active species are present in the medium to be investigated. For point-of-care diagnostic purposes, the complex mediums are tissue or biological fluids, such as saliva, blood, and urine. Thus, for detecting a particular molecule of interest, such as AHL, further separation or increased sensitivity towards the molecule of interest is needed.

Biological fluids are in addition complicated to investigate, since the amounts and types of electroactive species present in a sample will vary from one individual to another. Thus, for detecting a particular molecule of interest within biological fluid of an individual, different threshold values may apply to different persons.

The sensitivity of an electrochemical method may be improved by using additional electrodes, or increasing the electrode surface. In this case, the improved sensitivity is directly related to the higher reaction contact area, and thus increased signal. The improvement is therefore statistically based, and not based on a more efficient and/or more sensitive method. However, for practical and design reasons, electrochemical sensors with large dimensions are not desirable. This will especially be relevant, for point-of-care diagnostic purposes, where the general physician or the patient him/herself carry out the measurement.

US 2008/0249391 A1 [3] discloses a carbon electrode array for detecting neurotransmitter concentration in vivo, where the sensitivity is increased by increasing the surface of the carbon electrodes.

For diagnostic purposes, and particularly point-of-care diagnostic purposes, there is a need for devices that are capable of detecting and quantifying quorum sensing molecules, such as AHL that are indicators for bacterial virulent behavior, within a biological sample with high precision, and in a fast and simple way.

SUMMARY OF INVENTION

The present invention relates to an electrochemical device capable of detecting and quantifying quorum sensing molecules, which are indicators for bacterial virulent behavior, within a biological sample with high precision and with fast detection time. The present invention is preferably related to an electrochemical device and a method for detecting the presence of AHL in a biological sample.

A first aspect of the invention relates to an electrochemical device, comprising:
at least one reference electrode (RE),
at least one counter electrode (CE),
two or more working electrodes (WEs),
wherein each working electrode differ from the other working electrode(s) with respect to at least one of the following characteristics: surface area, size, material, and coating, a sample receiving area for receiving a biological sample, wherein the electrodes and the sample receiving area is fluidly connected
means for transferring the sample to the electrodes for measurement, and
means for displaying a result of the measurement.

Advantageously, the electrochemical device comprises:
two or more reference electrodes (REs),
two or more counter electrodes (CEs),
two or more working electrodes (WEs),
wherein the electrodes are arranged as two or more three-electrode cell sensors, wherein each three-electrode cell sensor has a RE, CE, and WE,
thereby forming an array of two or more three-electrode cell sensors.

Preferably, the device comprises an array of three sensors, and more preferably four, five or six sensors.

The electrochemical device may have several uses, and may be used for at least two methods.

A second aspect of the invention relates to a method for detecting the presence of a predetermined quorum sensing molecule in a biological sample, comprising the steps of:
providing an electrochemical device, comprising at least one reference electrode (RE), at least one counter electrode (CE), two or more working electrodes,
wherein each working electrode differ from the other working electrode(s) with respect to at least one of the following characteristics: surface area, size, material, and coating,
providing the biological sample to the electrodes,
applying voltammetry to the electrodes,
detecting a signal correlatable to the predetermined quorum sensing molecule for each of the sensors, and
optionally displaying a result of the measurement,
whereby the presence of a predetermined quorum sensing molecule is detected.

Preferably, the electrochemical device provided in the second aspect of the invention comprises two or more REs, two or more CEs, two or more WEs, wherein the electrodes are arranged as two or more three-electrode cell sensors, wherein each three-electrode cell sensor has a RE, CE, and WE.

Advantageously, the electrochemical device provided in the second aspect of the invention comprises an array of three sensors, and more preferably four, five or six sensors.

A third aspect of the invention relates to a method for measuring a level of a predetermined quorum sensing molecule in a biological sample, comprising the steps of:
providing an electrochemical device, comprising at least one reference electrode (RE), at least one counter electrode (CE), two or more working electrodes,
wherein each working electrode differ from the other working electrode(s) with respect to at least one of the following characteristics: surface area, size, material, and coating,
providing the biological sample to the electrodes,
applying voltammetry to the at least first WE,
applying chronoamperometry to the at least second WE,
detecting a signal from voltammetry correlatable to the predetermined quorum sensing molecule,
correlating the signal from chronoamperometry to a concentration,
whereby the level of the predetermined quorum sensing molecules is detected.

Preferably, the electrochemical device provided in the third aspect of the invention comprises two or more REs, two or more CEs, two or more WEs, wherein the electrodes are arranged as two or more three-electrode cell sensors, wherein each three-electrode cell sensor has a RE, CE, and WE.

Advantageously, the electrochemical device provided in the third aspect of the invention comprises an array of three sensors, and more preferably four, five or six sensors.

DESCRIPTION OF DRAWINGS

The invention will in the following be described in greater detail with reference to the accompanying drawings.

Figure 2:
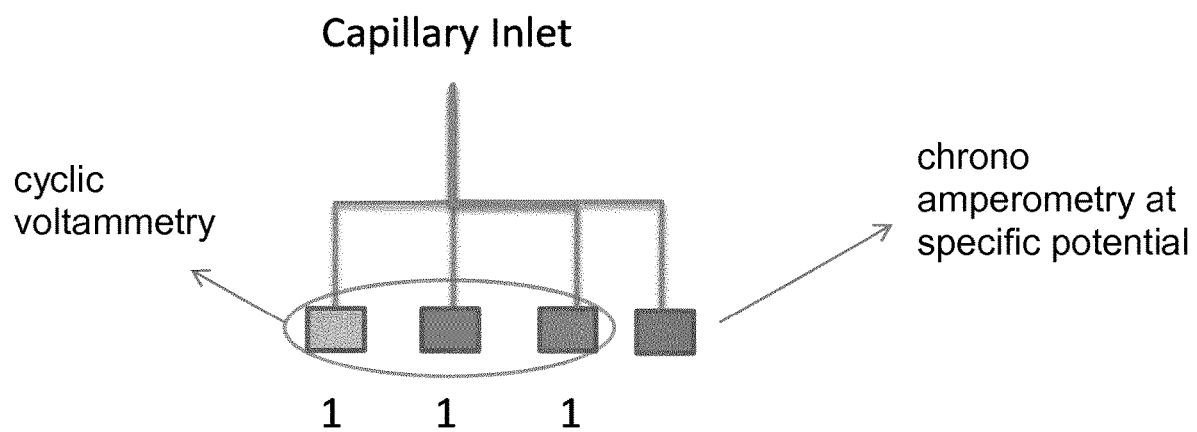
FIG. 2 shows a schematic of an embodiment of a device comprising four sensors, where three of the sensors are used for detecting the presence of AHL (detection sensors), and one sensor is used for quantification of AHL (quantification sensor) if the sample is AHL positive. The device further comprises a microfluidic system for transferring a biological sample from a sample receiving area to the array of sensors. In an embodiment of the device in FIG. 2, the four sensors (shown as squares) each comprises of a reference electrode (RE), a counter electrode (CE), and a working electrode (WE). The three electrodes of each sensor are not shown within each square of FIG. 2. Thus in this embodiment, the first sensor comprises a first RE, a first CE, and a first WE; the second sensor comprises a second RE, a second CE, and a second WE; the third sensor comprises a third RE, a third CE, and a third WE; and the fourth sensor comprises a fourth RE, a fourth WE. In a preferred embodiment, the four WEs will be different from each other. In another preferred embodiment, at least two of the WEs will be different from each other.

In another embodiment of the device in FIG. 2, the four sensors each comprise of a WE and optionally a CE (not shown in FIG. 2). The four sensors share a common RE and optionally a common RE, which may be electrically connected to the four sensors (the squared in FIG. 2) in a similar manner as illustrated for the capillary inlet.

Figure 3:
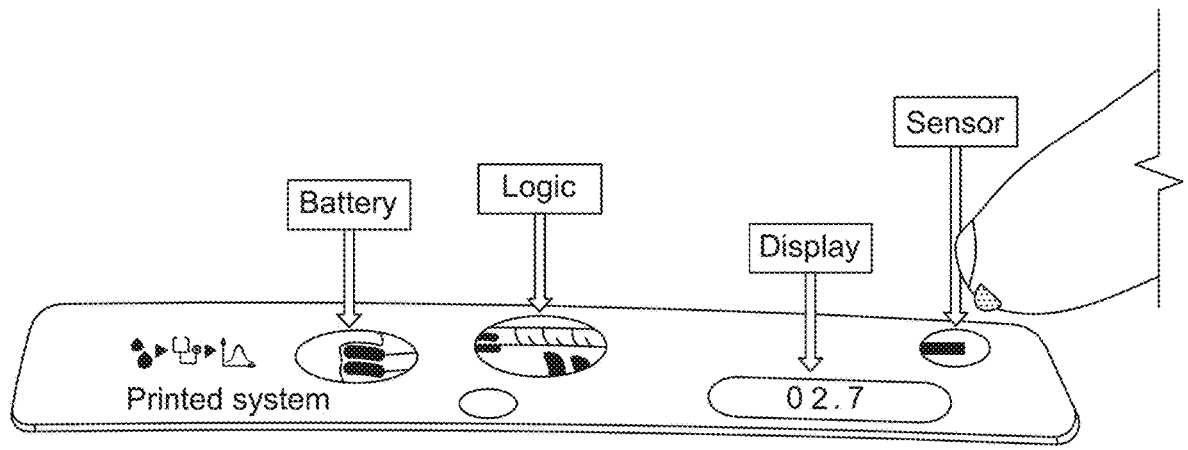

FIG. 3 shows an embodiment of an integrated device, comprising an array of sensors (not shown) fluidly connected to a sample receiving area, and means for displaying a result from the electrodes.

Figure 4:
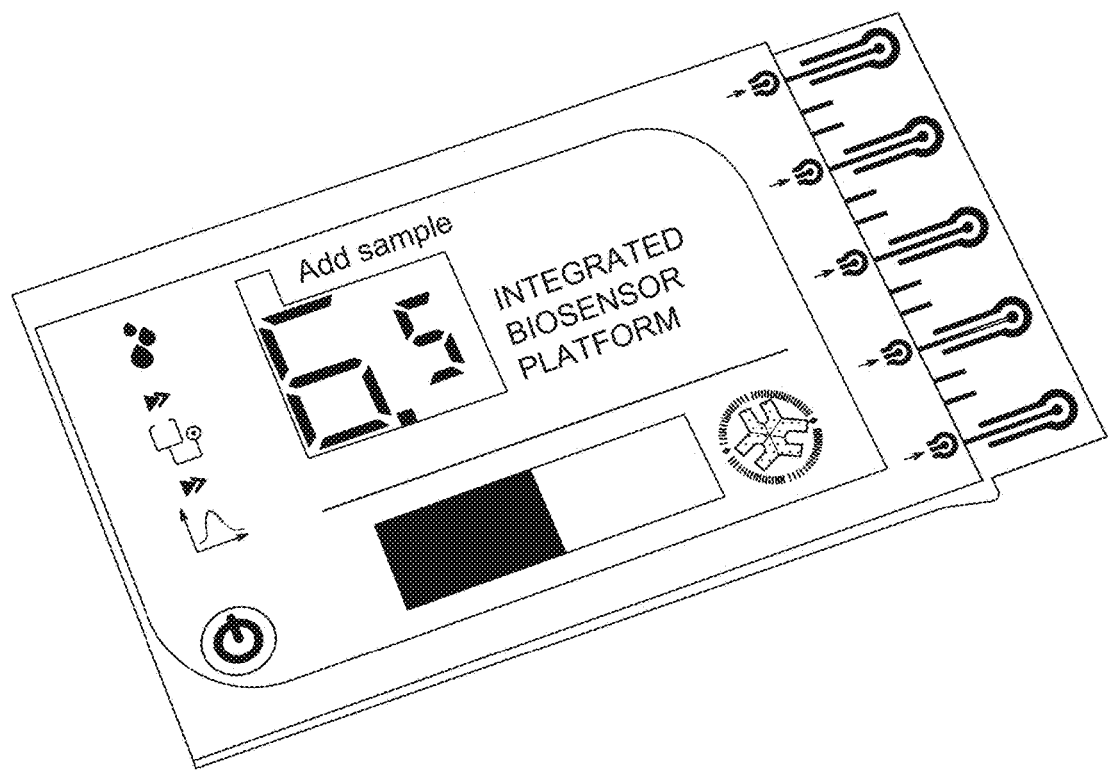
Figure 5A:
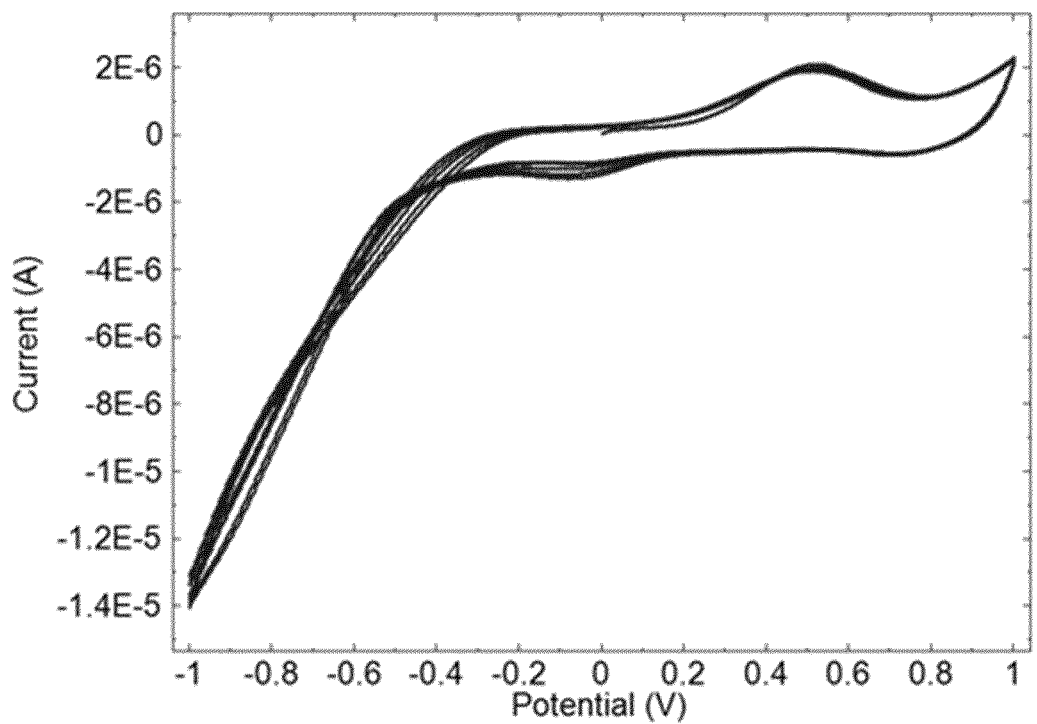
Figure 5B:
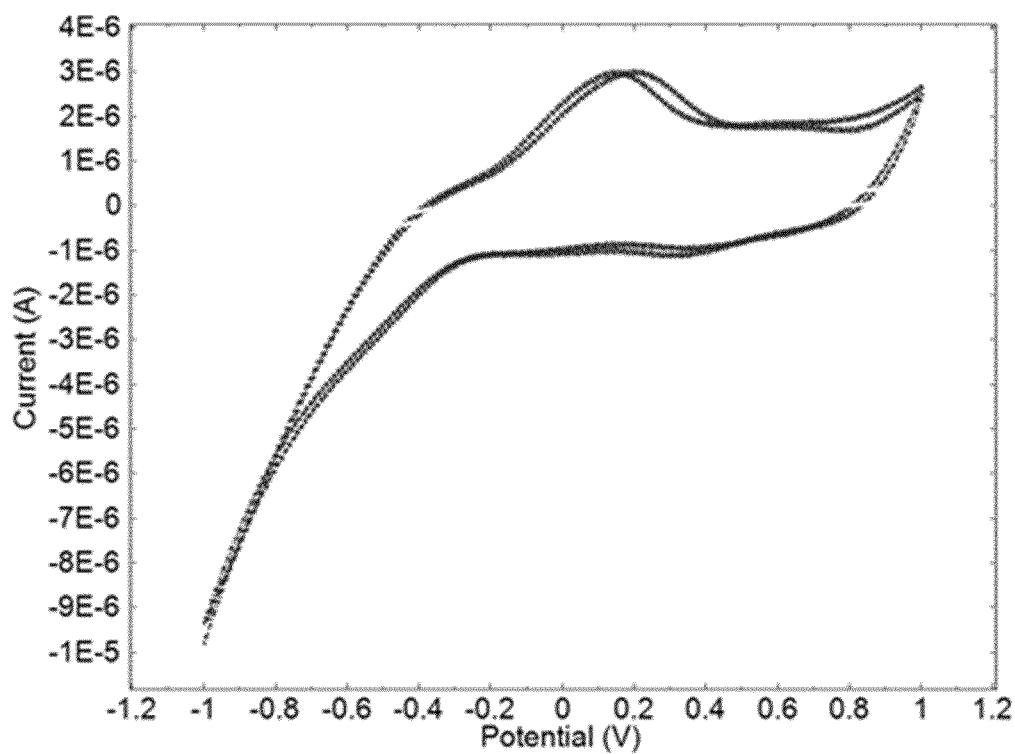
Figure 5C:
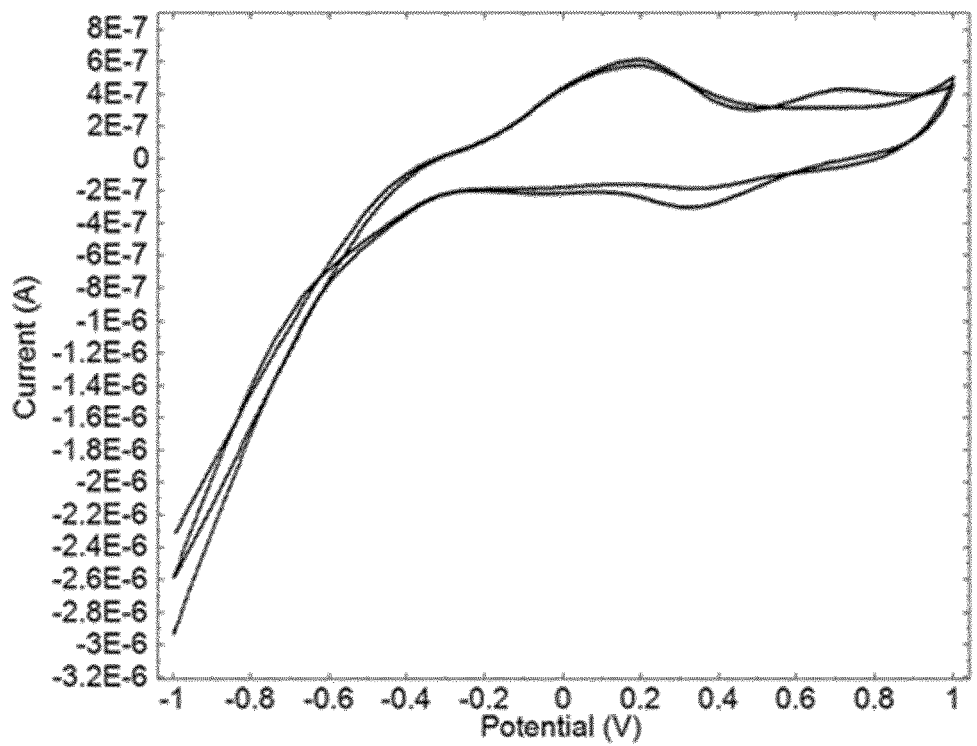
Figure 5D:
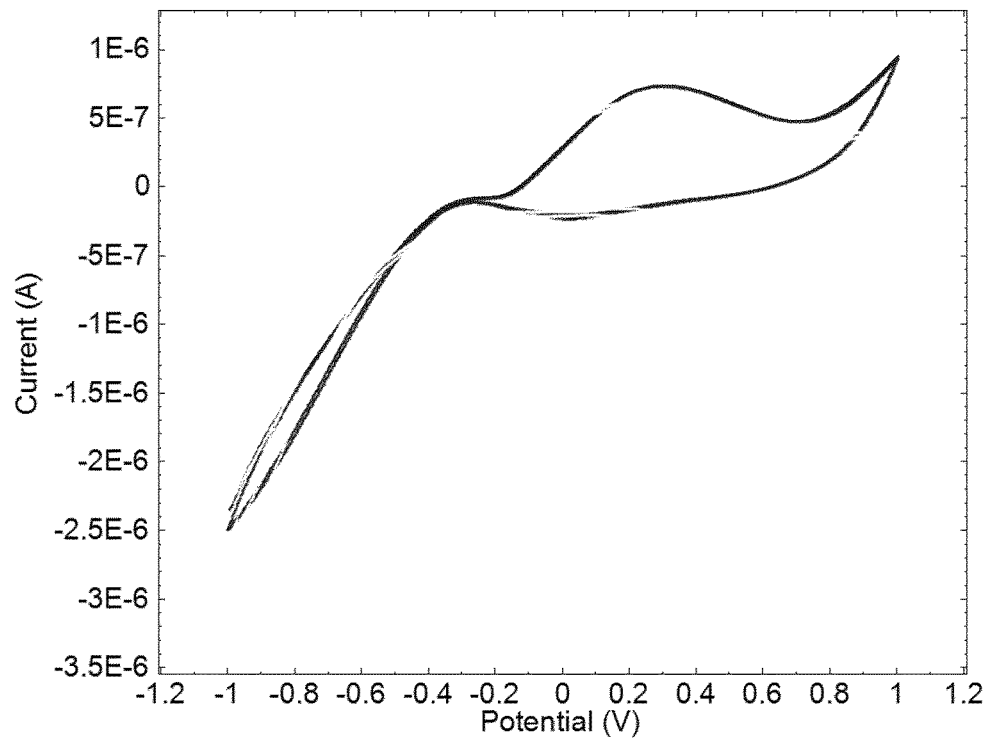

FIG. 4 shows an embodiment of an integrated device, comprising an array of sensors (not shown) fluidly connected to a sample receiving area, and means for displaying a result from the electrodes.

FIG. 5 shows cyclic voltammograms for AHL in water using a device comprising four sensors, wherein the four sensors are sensors with different working electrodes: (a) Sensor 1, with a working electrode of 1.6 mm Au screen-printed at elevated temperature, (b) Sensor 2, with a working electrode of 1.6 mm Pt, (c) Sensor 3, with a working electrode of 4 mm Au, and (d) Sensor 4, with a working electrode of 1.6 mm Au screen-printed at low temperature.

Figure 6:
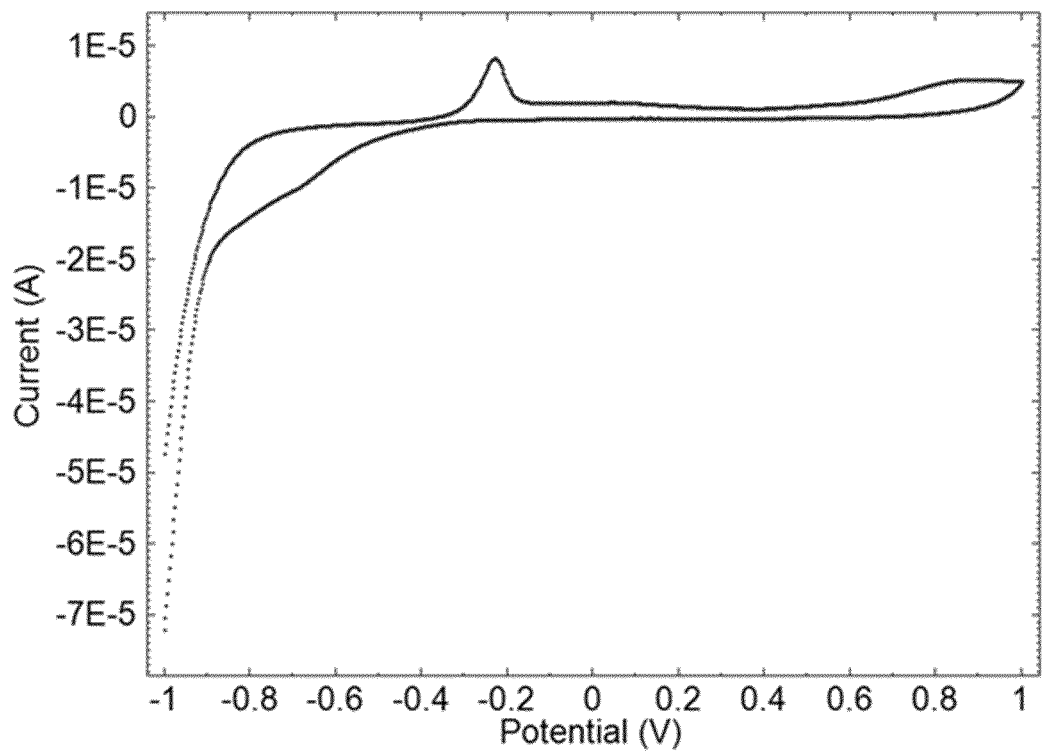

FIG. 6 shows cyclic voltammograms for a sputum sample using sensor 1 with a working electrode of 1.6 mm diameter gold.

Figure 7:
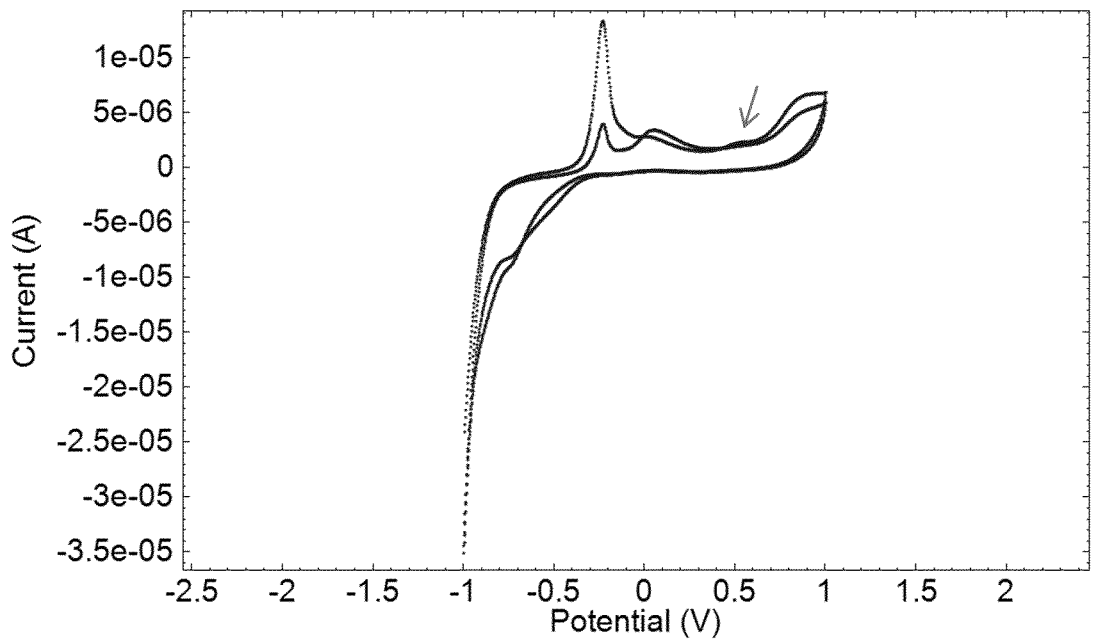

FIG. 7 shows cyclic voltammograms for a sputum sample using sensor 2 with a working electrode of 1.6 mm diameter platinum.

FIG. 8 shows the results from Example 3, where (a) shows the measured amperometric recording from 0-200 seconds, and (b) shows a calibration curve for $s_{std}$ as a function of $c_{std}$.

Figure 9:
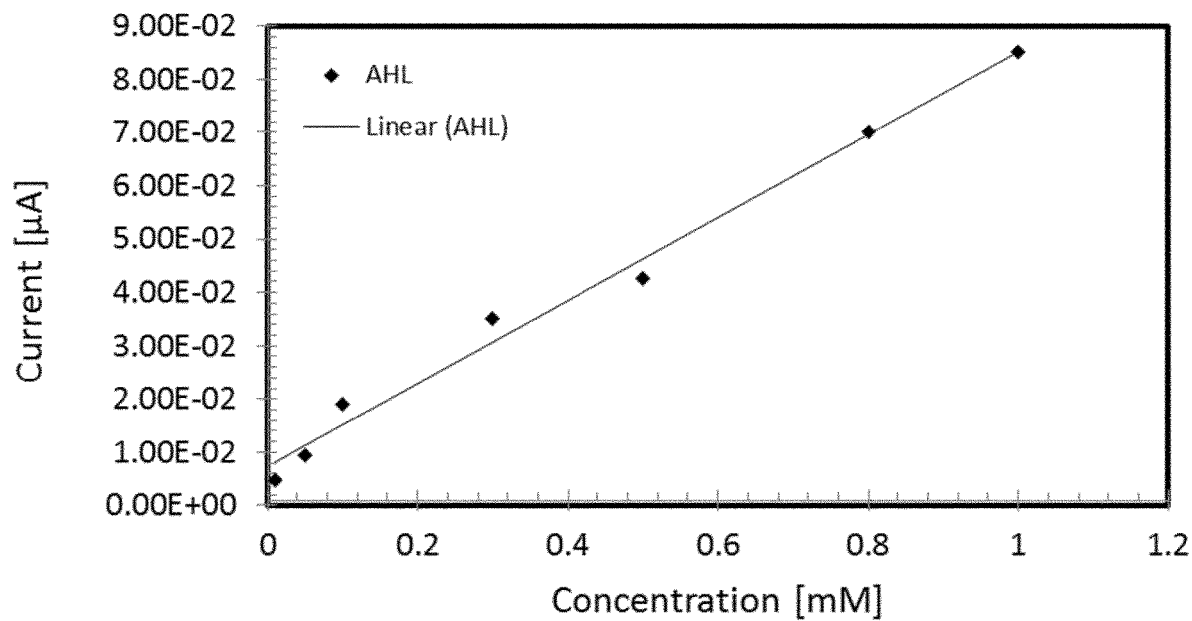

FIG. 9 shows the linear proportionality between the measured current and the AHL concentration for a dilution series of AHL in artificial sputum medium, measured by a fresh carbon sensor using square wave voltammetry, where the carbon sensor was part of a device comprising an sensor array, as described in Example 5.

Figure 10:
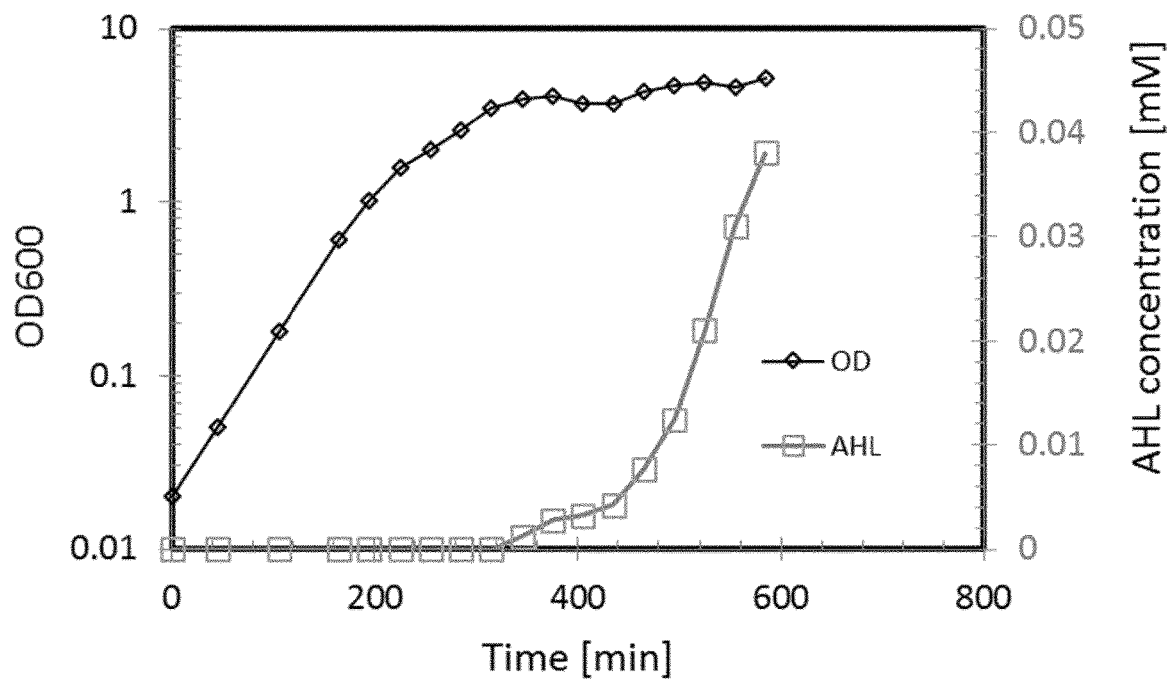

FIG. 10 shows the AHL production as function of bacterial growth (*Pseudomonas aeruginosa*, strain PAO1, cultured in LB medium, with growth measured by OD600), where the AHL concentration was measured by the device according to Examples 1 and 4, as described in Example 6.

DETAILED DESCRIPTION OF THE INVENTION

Figure 1A:
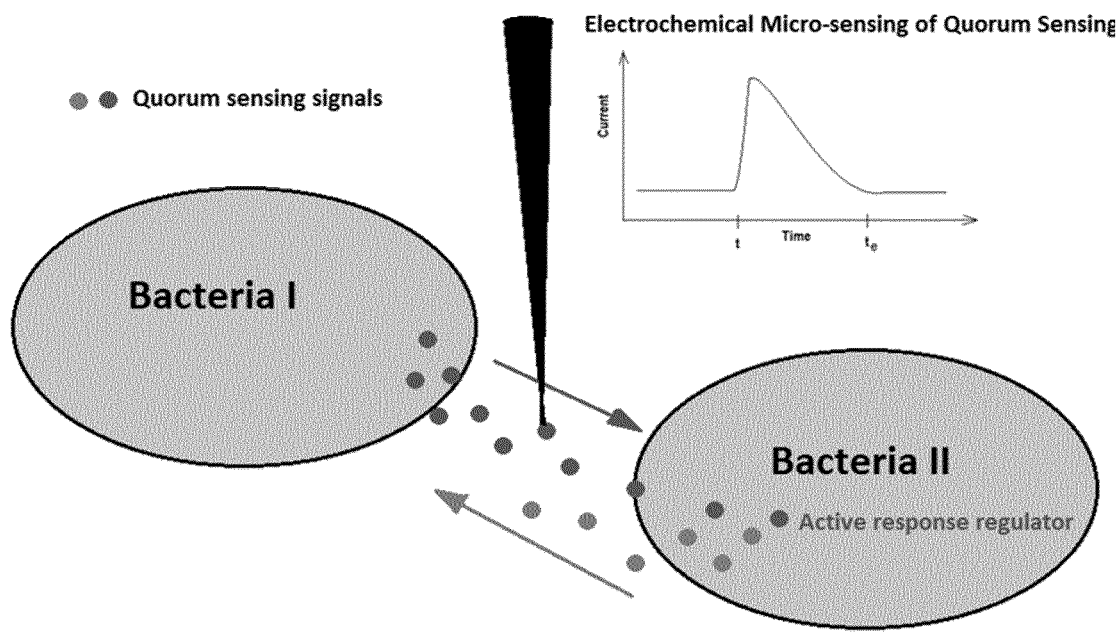
FIG. 1A shows a schematic of two bacteria producing quorum sensing molecules, whereby the bacteria communicate, and an electrode placed in the medium comprising the quorum sensing molecules. The medium is subjected to an increasing potential over time, indicated by the x-axis, and the current detected by the electrode is indicated by the y-axis in the voltammogram.

FIG. 1A shows a schematic of two bacteria producing quorum sensing molecules (shown as dots), whereby they communicate.

Quorum sensing molecules which may be indicators for bacterial virulent behavior include N-Acryl homoserine lactones (AHL), pyocyanin, 2-heptyl-3,4-dihydroxyquinoline (PQS), and 4-hydroxy-2-heptylquinoline (HHQ). As example, the general chemical structure of AHL is shown below, where R indicates an alkyl group side chain.

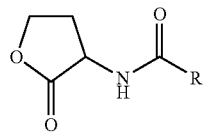

The embodiments of the invention described in the following may be extended to any quorum sensing molecule. However, in the following the embodiments are exemplified based on AHL.

When a quorum sensing molecule such as AHL is subjected to an increasing potential, the molecule will at some point become oxidized or reduced. The points where oxidation or reduction occur are also called respectively, the oxidation potential and reduction potential, or the redox potential.

At the oxidation potential, the released electrons from the AHLs may be detected as a current. FIG. 1A shows an electrode placed in the medium with quorum sensing molecules, where the medium is subjected to an increasing potential over time, indicated by the x-axis in the voltammogram of FIG. 1A, also shown magnified in FIG. 1B. At the oxidation potential, the electrode will detect a current peak, as indicated by the y-axis in the graph of FIGS. 1A-B.

Figure 1B:
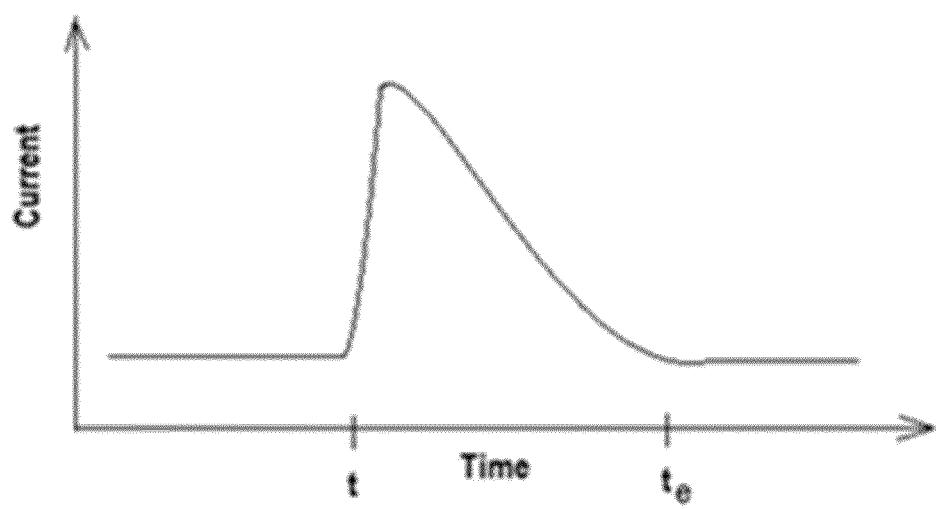
FIG. 1B shows a magnification of the voltammogram in FIG. 1A.

However, the graph of FIG. 1B also shows that the current generated by a medium comprising quorum sensing molecules is not restricted to a specific potential, but occurs over a range of potentials, as indicated by the time interval "t" to "$t_e$" in FIG. 1, and thus defines a current peak shape.

The current detected by the electrode in FIGS. 1A-B is generated by all the electro-active species that are adsorbed to the electrode surface. Thus, the shape of the current peak may reflect different electro-active species with similar oxidation potentials, as well as variation in the adsorption mechanism of a particular specie.

The quorum sensing molecule(s) are detected directly in the biological sample as discussed below. As discussed above, biological samples varies among individuals with respect to their amounts and types of electroactive species, and accordingly, biological samples are not standardized with respect to their content. Thus, for each individual, the shape of the current peak will be different, and a simple and general method to separate the background signal, from the signal from potentially present AHL, is not possible. A precise and efficient detection of a specific electro-active specie, such as AHL, is therefore not possible from a single electrode measurement.

Electrochemical Detection of Predetermined Quorum Sensing Signals

In the present invention it was found that a precise and efficient detection of a predetermined quorum sensing molecule can be obtained by use of a multiple of electrodes or sensors, comprising a reference electrode (RE), a counter electrode (CE), and two or more working electrodes (WEs).

The use of multiple of electrodes or sensors facilitates improved selectivity sensitivity of the quorum sensing molecule, e.g. AHL. Thus, the improved sensitivity is obtained by improved selectivity towards AHL, and not a statistical improvement merely related to an improved signal strength. By the term "selectivity sensitivity" is therefore meant improved sensitivity due to improved selective detection of AHL, i.e. AHL is detected selectively by different electrodes. The multiple detection electrodes or sensors may be incorporated into a single device, whereby a precise and efficient detection may be obtained from a single sample, i.e. as one measurement.

Advantageously, the multiple of electrodes, comprises two or more REs, two or more CEs, and two or more WEs, and further advantageously, the electrodes are arranged as two or more three-electrode cells, wherein each three-electrode cell has a RE, CE, and WE.

Any embodiment of the invention described in the following may be extended to both the embodiment comprising a multiple of electrodes, and the embodiment comprising electrodes arranged in three-electrode cells, forming an array of sensors. The following description is exemplified based on the embodiment comprising a sensor array.

In the present invention it was found that a precise detection of a predetermined quorum sensing molecule can be obtained by use of an array of three-electrode cell sensors, wherein each sensor is a three-electrode setup, and wherein each sensor comprises a working electrode that differs from the other working electrodes with respect to at least one of the following characteristics: surface area, size, material, and coating.

By the term "sensor" as used herein is meant a three-electrode cell setup consisting of a working electrode, counter electrode, and reference electrode. The terms "three-electrode cell sensor", "three-electrode cell", and "sensor" all refer to a sensor within the present definition.

A three-electrode setup may be used for measuring an electrochemical reaction taking place at the working electrode at a well-defined potential. In a three-electrode cell, the defined potential of the working electrode may be varied, and the response from the electrochemical reaction is seen from the current of the working electrode.

In cyclic voltammetry, the working electrode potential is ramped linearly versus time. The potential is ramped linearly up, and when a set potential is reached, the potential is ramped in the opposite direction to the initial potential, and the cycle is repeated. Other systematic variations of working electrode potential include linear sweep voltammetry, staircase voltammetry, squarewave voltammetry, and differential pulse voltammetry.

The use of a sensor array facilitates an electrochemical detection of predetermined quorum sensing molecules. The sensor array increases the sensitivity and specificity of the measurement, and reduces the noise from other substances present in a biological sample.

A sensor array comprises two or more sensors, wherein each sensor comprises a working electrode that differs from the other working electrodes with respect to at least one of the following characteristics: surface area, size, material, and coating.

A given quorum sensing chemical, such as AHL, will react electrochemically different on different electrode surfaces. Thus, different electrode materials and geometries used for chemical detection will give different results. In the present invention it was found that the combination of electrochemical responses from different working electrodes, can be used to detect the presence/absence (i.e. positive/negative results) of e.g. AHL in a sample with high precision. Furthermore, for a e.g. AHL positive sample, the present invention provides a method for detecting the concentration of AHL with high precision.

The different and distinctive AHL response obtained for sensors with different working electrodes are further described in Examples 1 and 2.

Predetermined Quorum Sensing Signals

The method for detection and quantification is exemplified for the communication molecule N-Acyl homoserine lactone (AHL), known to be released by bacteria prior to virulent behavior in the human body AHL. However, the method may also be applicable for other quorum sensing molecules, which are indicators for bacterial virulent behavior, such as pyocyanin, 2-heptyl-3,4-dihydroxyquinoline (PQS), and 4-hydroxy-2-heptylquinoline (HHQ).

Device

FIG. 2 shows a schematic of an embodiment of a device comprising four sensors, where three of the sensors are used for detecting the presence of AHL (detection sensors), and one sensor is used for quantification of AHL (quantification sensor) if the sample is AHL positive. The device further comprises means for transferring a biological sample from a sample receiving area to the array of sensors.

In an embodiment of the device in FIG. 2, the four sensors (shown as squares) each comprises of a reference electrode (RE), a counter electrode (CE), and a working electrode (WE). The three electrodes of each sensor are not shown within each square of FIG. 2. Thus in this embodiment, the first sensor comprises a first RE, a first CE, and a first WE; the second sensor comprises a second RE, a second CE, and a second WE; the third sensor comprises a third RE, a third CE, and a third WE; and the fourth sensor comprises a fourth RE, a fourth WE. In a preferred embodiment, the four WEs will be different from each other. In another preferred embodiment, at least two of the WEs will be different from each other.

In another embodiment of the device in FIG. 2, the four sensors each comprise of a WE and optionally a CE (not shown in FIG. 2). The four sensors share a common RE and optionally a common RE, which may be electrically connected to the four sensors (the squares in FIG. 2) in a similar manner as illustrated for the capillary inlet.

Advantageously, the same sensor is used as quantification sensor during repeated use of the electrochemical device.

The biological sample to be tested for AHL is placed at the sample receiving area indicated by the capillary inlet in FIG. 2. The biological sample may be any body fluid, such as blood, saliva, urine, sputum, broncho alveolar liquid, or tissue, and the biological sample may be as in vivo, or pretreated, such as dissolved or diluted.

The biological sample may be a patient sample of a few microliters. When a sample is placed at the capillary inlet, the sample is distributed and transferred to each sensor in the array by a microfluidic system e.g. capillary forces or pumping means. Thus, the capillary inlet branch to different channels, where each is directed to a sensor. This further prevents cross-contamination between the sensors.

The device may be integrated into a portable device. FIGS. 3 and 4 shows embodiments of integrated devices, comprising an array of electrodes (not shown) fluidly connected to a sample receiving area, and where the devices further comprise means for displaying a result from the electrodes.

In an embodiment of the invention, the sample receiving area is configured to biological samples, such as body fluids selected from the group consisting of: blood, saliva, urine, sputum, dissolved tissue, and broncho alveolar liquids.

In another embodiment of the invention, the means for transferring the sample to the array of sensors is a capillary network.

In another embodiment, the device further comprises means for displaying a result of the measurement, such as a display or a user interface.

Detection Sensors

When the biological sample in FIG. 2 reaches the sensors, each working electrode is subjected to a potential sweep, e.g. cyclic voltammetry. Thus, a predetermined potential range is applied on each of the detecting sensors.

Within the predetermined potential range, each working electrode may be calibrated based on the voltammogram obtained in the certain presence of AHL. Thus, the peak value that is obtained if AHL is present in the sample is known if the sensors are calibrated. For measurement on an unknown sample, a positive response for AHL is indicated if the potential peak value of the voltammogram is identical to the calibration value. A positive response for AHL is denoted with the value 1 (as shown in FIG. 2), and a negative response for AHL is denoted with the value 0.

Thus, for the embodiment shown in FIG. 2, a positive response for AHL can be established if three sensors have the value 1, corresponding to a sum value of 3. In a preferred embodiment of the invention, a positive response for AHL may be established based on a sum value of 3 from the multiple sensors, and a negative response for AHL may be established based on a sum value below 3.

However, as some molecules might be similar to AHL and also present in the biological sample, a positive response peak from a single sensor cannot be used to determine if AHL is present with high certainty.

The calibration voltammogram will depend on the shape and material of the working electrode, since the AHL molecule will react differently with different electrodes. Thus, when the potential scan is applied to the array of sensors, each sensor will give an independent value for the presence or absence of AHL.

In the present invention it was found that a target compound can be distinguished with high certainty by use of a sensor array comprising at least two sensors, where the sensors comprises different working electrodes. However, the higher the number of detecting sensors, the higher the statistical significance of the result.

In an embodiment of the invention, the array comprises three sensors, and more preferably four, five or six sensors.

In a preferred embodiment, the array comprises three sensors as illustrated in FIG. 2. Each of the sensors gives a value of 1 if the expected AHL peak is found, and the value is 0 if the expected AHL peak is not found. The presence of AHL is precisely detected, if all sensors gives a positive response for AHL. Thus, if the sum of the obtained values equals the sum of the detecting sensors, the presence of AHL can be confirmed.

The different and distinctive AHL response obtained for sensors with different working electrodes are further described in Examples 1 and 2.

In an embodiment of the invention, the method for detecting the presence of a predetermined quorum sensing molecule in a biological sample, comprises the steps of:
providing an array of least two sensors,
wherein each sensor is a three-electrode cell comprising a working electrode, counter electrode, and reference electrode,
wherein the working electrode of each sensor differ from the other working electrode(s) with respect to at least one of the following characteristics: surface area, size, material, and coating,
providing the biological sample to the array of sensors,
applying voltammetry to the sensors,
detecting a signal correlatable to the predetermined quorum sensing molecule for each of the sensors, and
optionally displaying a result of the measurement,
whereby the presence of a predetermined quorum sensing molecule is detected.

In another embodiment of the invention, the method for detecting the presence of a predetermined quorum sensing molecule in a biological sample, comprising the steps of:
providing an electrochemical device, comprising at least one reference electrode (RE), at least one counter electrode (CE), two or more working electrodes,
wherein each working electrode differ from the other working electrode(s) with respect to at least one of the following characteristics: surface area, size, material, and coating,
providing the biological sample to the electrodes,
applying voltammetry to the electrodes,
detecting a signal correlatable to the predetermined quorum sensing molecule for each of the sensors, and
optionally displaying a result of the measurement,
whereby the presence of a predetermined quorum sensing molecule is detected In a further embodiment, the electrochemical device comprises two or more REs, two or more CEs, two or more WEs, wherein the electrodes are arranged as two or more three-electrode cell sensors, wherein each three-electrode cell sensor has a RE, CE, and WE. In a further embodiment, the electrochemical device comprises an array of three sensors, and more preferably four, five or six sensors.

In an embodiment of the invention, the quorum sensing molecule is selected from the group consisting of: AHL, pyocyanin, PQS, and HHX.

In an embodiment of the invention, the voltammetry is selected from the group consisting of: linear sweep voltammetry, staircase voltammetry, square wave voltammetry, differential pulse voltammetry and cyclic voltammetry, and more preferably is cyclic voltammetry and square wave voltammetry.

Quantification Sensor

For an AHL positive sample, the content of AHL can be determined by use of any of the sensors. However, advantageously, the content of AHL is determined by use of a separate and dedicated sensor (the quantification sensor) as shown in FIG. 2.

Similarly to the three detection sensors in FIG. 2, the quantification sensor is a three electrode setup. However, the quantification sensor is operated at a constant potential, i.e. using chronoamperometry, whereas the detection sensors are operated at a variable (e.g. cyclic) potential.

The constant potential is configured by calibration such that only AHL molecules are electrochemically detected at this characteristic potential. Thus, even though molecules similar to AHL may be electrochemically active at the constant potential, their contribution is not included due to the calibration. Therefore, at the characteristic potential, the charge accumulation that can be extracted from the measurement is directly proportional to the AHL concentration, and the AHL content in the sample can be determined.

The quantification of AHL using a quantification sensor is further described in Example 3.

In an embodiment of the invention, the method for measuring a level of a predetermined quorum sensing molecule in a biological sample, comprises the steps of:
providing an array of least three sensors,
wherein each sensor is a three-electrode cell comprising a working electrode, counter electrode, and reference electrode,
wherein the working electrode of each sensor differ from the other working electrode(s) with respect to at least one of the following characteristics: surface area, size, material, and coating,
providing the biological sample to the array of sensors,
applying voltammetry to the at least two sensors,
applying chronoamperometry to at least one sensor,
detecting a signal correlatable to AHL for each sensor,
correlating the signal from chronoamperometry to a concentration,
whereby the level of the predetermined quorum sensing molecules is detected.

In another embodiment of the invention, the method for measuring a level of a predetermined quorum sensing molecule in a biological sample, comprising the steps of:
providing an electrochemical device, comprising at least one reference electrode (RE), at least one counter electrode (CE), two or more working electrodes,
wherein each working electrode differ from the other working electrode(s) with respect to at least one of the following characteristics: surface area, size, material, and coating,
providing the biological sample to the electrodes,
applying voltammetry to the at least first WE,
applying chronoamperometry to the at least second WE,
detecting a signal from voltammetry correlatable to the predetermined quorum sensing molecule,
correlating the signal from chronoamperometry to a concentration,
whereby the level of the predetermined quorum sensing molecules is detected.

In a further embodiment, the electrochemical device comprises two or more REs, two or more CEs, two or more WEs, wherein the electrodes are arranged as two or more three-electrode cell sensors, wherein each three-electrode cell sensor has a RE, CE, and WE. In a further embodiment, the electrochemical device comprises an array of three sensors, and more preferably four, five or six sensors.

In an embodiment of the invention, the quorum sensing molecule is selected from the group consisting of: AHL, pyocyanin, PQS, and HHX.

In an embodiment of the invention, the chronoamperometry is carried out at a specific potential between 0.05-0.40 V, more preferably between 0.10-0.20 V, and most preferably the specific potential is 0.19 V.

Electrodes

Advantageously, the working electrodes are electrodes that show a distinctive voltammogram with respect to the AHL electrochemical reaction.

Distinctive voltammogram peaks for the AHL reaction may be obtained with working electrodes comprising a material selected from the group of: gold (Au), silver (Ag), platinum (Pt), ITO, P-dot, carbon, multiwalled carbon nanotubes, singlewalled carbon nanotubes, carbon nanofibers, graphene, carbon-platinum composites, multiwalled carbon nanotubes with gold nanoparticles, and any combination thereof.

By the term "ITO" is meant Optically Transparent Indium tin oxide

By the term "PEDOT" is meant Poly(3,4-ethylenedioxythiophene) or simply polymer.

In an embodiment of the invention the working electrode material of one or more sensors is selected from the group consisting of: gold (Au), silver (Ag), platinum (Pt), ITO, P-dot, carbon, multiwalled carbon nanotubes, singlewalled carbon nanotubes, carbon nanofibers, graphene, carbon-platinum composites, multiwalled carbon nanotubes with gold nanoparticles, and any combination thereof.

Distinctive voltammogram peaks for AHL may further be obtained with working electrodes of different sizes and/or surface areas. Furthermore, distinctive voltammogram peaks may be obtained with working electrodes made by different fabrication procedures. For example, the electrodes may be fabricated by screen-printing, such as screen printing at elevated temperatures, or low temperatures.

In an embodiment of the invention, the working electrode of one or more sensors has a diameter between 0.1-10 mm, more preferably between 1-5 mm, and most preferably a diameter of 1.6 mm or 4 mm.

In another embodiment of the invention, the device comprises an array of three sensors, wherein the first sensor has a working electrode of gold with a first diameter, the second sensor has a working electrode of gold with a second diameter, and the third sensor has a working electrode of platinum.

In a further embodiment, the device further comprises a fourth sensor with a working electrode of carbon.

Any counter electrode and reference electrode that are compatible with the chosen working electrode may be used.

Advantageously, the counter electrode is of the same material and type as the working electrode.

In an embodiment of the invention, the counter electrode of each sensor is identical to the working electrode of said sensor.

In an embodiment of the invention, the reference electrode material of one or more sensors is selected from the group consisting of: silver (Ag), silver chloride (AgCl), platinum (Pt) and more preferably is silver (Ag). In a preferred embodiment of the invention, the reference electrode of all sensors in the array is silver (Ag).

EXAMPLES

The invention is further described by the examples provided below.

Example 1: Electrochemical Detection of AHL with Different Sensors

Experimental

Synthetic AHL was diluted in artificial sputum as a model of an AHL positive patient sample. The sample was tested on different sensors, and the resulting cyclic voltammogram was recorded using a potential range of −1.0 to 1.0 V and a scan rate of 0.05 V/s. The same was repeated for artificial sputum without AHL.

The sensors were connected to a potentiostat (Metrohm Autolab, The Netherlands) from which cyclic voltammetry was used to characterize the electrochemical profile of AHL (804258, Aldrich, USA) diluted in water.

The software Autolab NOVA 1.11 (Metrohm Autolab, The Netherlands) was used for data handling, peak finding and analysis. Cyclic voltammetry was applied over a potential of −1.0 to 1.0 V and a scan rate of 0.05 V/s.

The four sensors were implemented within a device similar to the device illustrated in FIG. 2. The device comprises an array of four sensors, where each of the four sensors comprised a RE, a CE, and a WE, and where each of the four WEs were different, and optionally the REs and CEs were different. The electrodes of the four sensors are specified below.

Four different sensors were tested:

Sensor 1:

Disposable screen-printed electrodes with a three-electrode configuration were used for the electrochemical experiments (C223AT, Dropsens, Spain). The electrodes consisted of a 1.6 mm in diameter gold working electrode, a gold counter electrode and a silver reference electrode screen printed with high temperature.

Sensor 2:

Sensor consisting of a 1.6 mm in diameter platinum working and counter electrodes and a silver reference electrode (DRP-550, Dropsens, Spain).

Sensor 3:

Sensor consisting of gold working electrode of 4 mm in diameter, with gold counter and silver reference electrodes (C220AT, Dropsens, Spain).

Sensor 4:

Sensor consisting of 1.6 mm in diameter gold working and reference electrodes and silver reference electrodes screen print with low temperature (C223BT, Dropsens, Spain) were also used.

Results

FIG. 5 shows cyclic voltammograms for AHL in water using the four sensors with different working electrodes: (a) Sensor 1, with a working electrode of 1.6 mm Au screen-printed at elevated temperature, (b) Sensor 2, with a working electrode of 1.6 mm Pt, (c) Sensor 3, with a working electrode of 4 mm Au, and (d) Sensor 4, with a working electrode of 1.6 mm Au screen-printed at low temperature.

For example: A distinct oxidation peak was observed at 0.52 V using 1.6 mm gold electrodes, cf. FIG. 5a, while the detection using 4 mm gold electrodes gives a peak at 0.19 V, cf. FIG. 5c. It is seen how the different electrode material and different electrode size result in different peak values. The peak values are extracted and summarized in Table 1.

TABLE 1

Peak values extracted from FIGS. 5a-d.

| Sensor | Working electrode | Peak position (V) |
|---|---|---|
| 1 | 1.6 mm gold high temperature printed | 0.52 |
| 2 | 1.6 mm Platinum | 0.14 |
| 3 | 4 mm gold | 0.19 |
| 4 | 1.6 mm gold low temperature printed | 0.29 |

The results demonstrate that AHL can be detected with high accuracy using a biological sample without any pretreatment of the sample, and furthermore that AHL can be detected using an array of sensors, where the electrodes used for the measurements are not functionalized.

Example 2: Selective Electrochemical Detection of AHL

Experimental

A simulated sputum sample from a patient comprising AHL was provided. The sample was tested using a device comprising an array of two sensors, where the two sensors were different, and where the sensors were identical to sensors 1 and 2 in Example 1.

Results

FIG. 6 shows cyclic voltammograms for the sputum sample using sensor 1 with a working electrode of 1.6 mm diameter gold. The characteristic peak of AHL, was observed. Thus, sensor 1 gave a positive response for AHL, i.e. the value 1. A corresponding sputum sample without AHL would not display the characteristic peak, and only a similar background pattern without the peak would be seen.

FIG. 7 shows cyclic voltammograms for the sputum sample using sensor 2 with a working electrode of 1.6 mm diameter gold. The characteristic peak of 0.52 V was observed (indicated by arrow in FIG. 7). Thus, sensor 2 also gave a positive response for AHL, i.e. the value 1. A corresponding sputum sample without AHL would not display the characteristic peak, and only a similar background pattern without the peak would be seen.

Thus, the combined electrochemical profile of the artificial sputum resulted in a precise detection of the presence of AHL. Since the two different electrodes showed the AHL peak at their respective potential positions, the sum of the values is 2, and the presence of AHL can be confirmed. The results implies that AHL can be selectively detected on a biological sample without any pretreatment of the sample.

Example 3: Quantification of AHL

Experimental

A dilution series of AHL in water was prepared and measured by a fresh carbon sensor using a constant potential of 0.19 V. A sample of artificial sputum containing AHL was placed on the carbon sensor and a constant potential of 0.19 V was applied. The same was repeated with pure artificial sputum.

The carbon sensor may be comprised in an array of sensors, such as an array of sensors comprising the sensors of Examples 1 or 2. For example, the carbon sensor could be the fourth sensor, furthest to the right in FIG. 2, within the array of sensors exemplified in FIG. 2.

The carbon sensor consisted of a carbon working electrode, carbon counter electrode and silver reference electrode.

Amperometric measurements were obtained by recording the decay in signal from the electrochemical interaction between the sample and the electrodes. The amperometric signals were integrated between 0-200 seconds to obtain the accumulated charge.

Results

Figure 8A:
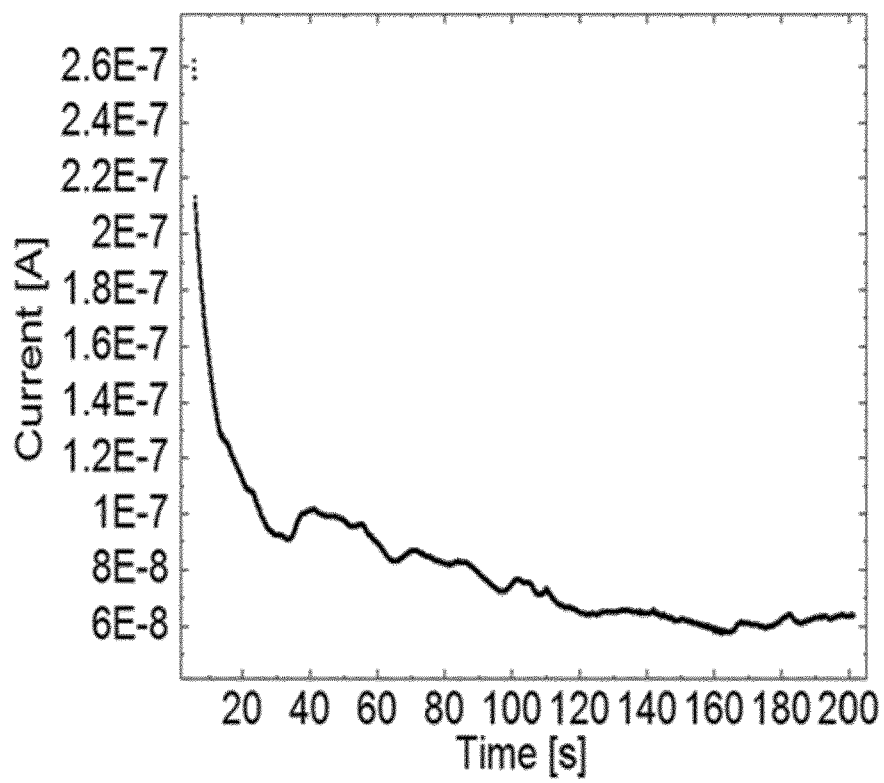

FIG. 8a shows the measured amperometric recording. The current was integrated from 0-200 seconds, and the actual concentration may then be determined from a calibration curve.

Figure 8B:
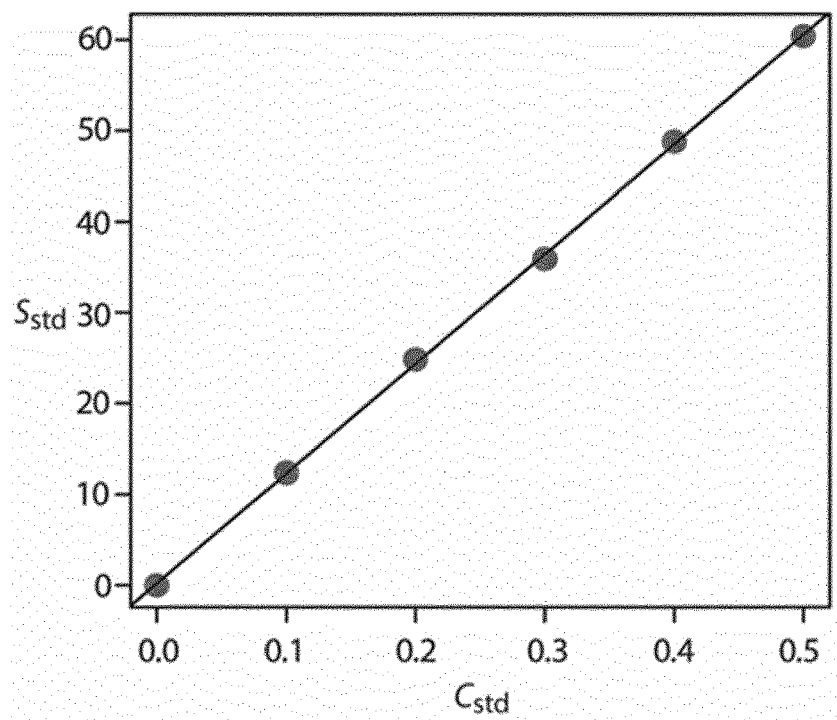

FIG. 8b shows a calibration curve, showing $s_{std}$ as a function of $c_{std}$. By the term "$s_{std}$" and "$c_{std}$" is meant signal and concentration, respectively.

The calibration curve can be obtained by integrating the graph measured at each concentration and plotting the obtained signals as function of their corresponding concentrations.

The results show that for an AHL positive sample, the concentration of AHL can be determined with high precision.

Example 4: Selective Electrochemical Detection of AHL with Different Sensors Experimental Synthetic AHL (804258, Aldrich, USA) was diluted in artificial sputum as a model of an AHL positive patient sample. Square wave voltammograms were recorded using a potential range of −1.0 to 1.0 V, an amplitude of 0.05 V and a frequency of 10 Hz. The same was repeated for artificial sputum without AHL. The sensors were connected to a potentiostat (Metrohm Autolab, The Netherlands) from which square wave voltammetry was used to characterize the electrochemical profile of AHL. The software Autolab NOVA 1.11 (Metrohm Autolab, The Netherlands) was used for data handling, peak finding and analysis.

A device similar to the device illustrated in FIG. 2 was applied, however, the device was equipped with five different sensors.

The five different sensors that were used for the detection of AHL:

Sensor 1:

Disposable in-house-made sensors with a three-electrode configuration were used for the electrochemical experiments. The electrodes consisted of a 1.6 mm in diameter gold working electrode and gold counter and reference electrode.

Sensor 2:

Sensor consisting of a 1.6 mm in diameter ITO working and counter electrodes and a silver reference electrode (ITO10, Dropsens, Spain).

Sensor 3:

Sensor consisting of carbon working electrode of 4 mm in diameter, with carbon counter and silver reference electrodes (110, Dropsens, Spain).

Sensor 4:

In-house made sensor consisting of 4 mm in diameter gold working electrode and gold counter and reference electrodes were also used.

Sensor 5:

Sensor consisting of PDOT working electrode of 4 mm in diameter, with carbon counter and silver reference electrodes (P10, Dropsens, Spain).

Results

The peak values are extracted and summarized in Table 2. Table 2 shows how the different electrode material and different electrode size result in different peak values.

TABLE 2

Peak values extracted from Example 4.

| | Electrode material | Detection potential |
|---|---|---|
| Sensor 1 | ITO | 0.576 V |
| Sensor 2 | 1.6 mm gold | 0.038 V |
| Sensor 3 | 4 mm gold | −0.191 V |
| Sensor 4 | PDOT | −0.303 V |
| Sensor 5 | Carbon | 0.410 V |

Another compound, pyoverdine, is also detected at 0.038 V using the 1.6 mm gold sensor (sensor 2).

In order to selectively distinguish between AHL and pyoverdine in blind samples we measured with sensors 1, 2, 3, 4 and 5 on samples comprising only pyoverdine. The resulting peak profile is as listed in Table 3:

TABLE 3

Peak values extracted from pyoverdine.

| | Electrode material | Detection potential of pyoverdine |
|---|---|---|
| Sensor 1 | ITO | 0.143 V |
| Sensor 2 | 1.6 mm gold | 0.038 V |
| Sensor 3 | 4 mm gold | 0.191 V |
| Sensor 4 | PDOT | 0.231 V |
| Sensor 5 | Carbon | 0.259 V |

The results demonstrate that the peak values are different from the values of AHL which means that we can use the sensor combinations to selectively detect AHL.

AHL can therefore be detected with high accuracy without any pretreatment of the sample, and furthermore that AHL can be detected using an array of sensors, where the electrodes used for the measurements are not functionalized.

Thus, the reason why we can be selective without functionalization is that we use a combination of sensors that have different materials and different dimensions. In addition, we have been able to electrochemically detect AHL which has never been reported.

Example 5: Quantification of AHL

Experimental

A dilution series of AHL in artificial sputum medium was prepared and measured by a fresh carbon sensor using square wave voltammetry. The peak height corresponds to the concentration of AHL.

The carbon sensor was one of the sensors in a device as illustrated in FIG. 2, comprising a multiple, or an array, of sensors.

Results

FIG. 9 shows the linear proportionality between the measured current and the AHL concentration.

The results show that for an AHL positive sample, the concentration of AHL can be determined with high precision.

Example 6: Selective Detection of AHL Secreted by Bacteria

Experimental

*Pseudomonas aeruginosa*, strain PAO1, were cultured in LB medium and growth was measured by OD600, while simultaneously measuring the AHL production using the device, or sensor array, described in examples 1 and 4. When AHL was determined by the array, the peak height was extracted to identify the concentration of the compound.

Results

FIG. 10 shows the AHL production as function of bacterial growth.

Items

The invention can be further described by the items listed below.

Item 1

An electrochemical device, comprising:
at least one reference electrode (RE),
at least one counter electrode (CE),
two or more working electrodes (WEs),
  wherein each working electrode differ from the other working electrode(s) with respect to at least one of the following characteristics: surface area, size, material, and coating,
a sample receiving area for receiving a biological sample,
  wherein the electrodes and the sample receiving area is fluidly connected
means for transferring the sample to the electrodes for measurement, and
means for displaying a result of the measurement.

Item 2

The electrochemical device according to item 1, further comprising:
two or more reference electrodes (REs),
two or more counter electrodes (CEs),
two or more working electrodes (WEs),
  wherein the electrodes are arranged as two or more three-electrode cell sensors, wherein each three-electrode cell sensor has a RE, CE, and WE, thereby forming an array of two or more three-electrode cell sensors.

Item 3

The device according to any of the preceding items, comprising an array of three sensors, and more preferably four, five or six sensors.

Item 4

The device according to any of the preceding items, wherein the reference electrode material of one or more sensors is selected from the group consisting of: silver (Ag), silver chloride (AgCl), platinum (Pt) and more preferably is silver (Ag).

Item 5

The device according to any of the preceding items, wherein the counter electrode of each sensor is identical to the working electrode of said sensor.

Item 6

The device according to any of the preceding items, wherein the working electrode material of one or more sensors is selected from the group consisting of: gold (Au), silver (Ag), platinum (Pt), ITO, P-dot, carbon, multiwalled carbon nanotubes, singlewalled carbon nanotubes, carbon nanofibers, graphene, carbon-platinum composites, multiwalled carbon nanotubes with gold nanoparticles, and any combination thereof.

Item 7

The device according to any of the preceding items, wherein the working electrode of one or more sensors has a diameter between 0.1-10 mm, more preferably between 1-5 mm, and most preferably a diameter of 1.6 mm or 4 mm.

Item 8

The device according to any of the preceding items, comprising an array of three sensors, wherein the first sensor has a working electrode of gold with a first diameter, the second sensor has a working electrode of gold with a second diameter, and the third sensor has a working electrode of platinum.

Item 9

The device according to item 7, further comprising a fourth sensor with a working electrode of carbon.

Item 10

The device according to any of the preceding items, wherein the sample receiving area is configured to biological samples, such as body fluids selected from the group consisting of: blood, saliva, urine, sputum, dissolved tissue, and broncho alveolar liquids.

Item 11

The device according to any of the preceding items, wherein the means for transferring the sample to the array of electrodes is a capillary network.

Item 12

The device according to any of the preceding items, wherein the means for displaying a result of the measurement is a display or a user interface.

Item 13

A method for detecting the presence of a predetermined quorum sensing molecule in a biological sample, comprising the steps of:
providing an electrochemical device, comprising at least one reference electrode (RE), at least one counter electrode (CE), two or more working electrodes,
wherein each working electrode differ from the other working electrode(s) with respect to at least one of the following characteristics: surface area, size, material, and coating,
providing the biological sample to the electrodes,
applying voltammetry to the electrodes,
detecting a signal correlatable to the predetermined quorum sensing molecule for each of the sensors, and
optionally displaying a result of the measurement,
whereby the presence of a predetermined quorum sensing molecule is detected.

Item 14

The method according to item 13, wherein the electrochemical device comprises two or more REs, two or more CEs, two or more WEs, wherein the electrodes are arranged as two or more three-electrode cell sensors, wherein each three-electrode cell sensor has a RE, CE, and WE.

Item 15

A method for measuring a level of a predetermined quorum sensing molecule in a biological sample, comprising the steps of:
providing an electrochemical device, comprising at least one reference electrode (RE), at least one counter electrode (CE), two or more working electrodes,
wherein each working electrode differ from the other working electrode(s) with respect to at least one of the following characteristics: surface area, size, material, and coating,
providing the biological sample to the electrodes,
applying voltammetry to the at least first WE,
applying chronoamperometry to the at least second WE,
detecting a signal from voltammetry correlatable to the predetermined quorum sensing molecule,
correlating the signal from chronoamperometry to a concentration,
whereby the level of the predetermined quorum sensing molecules is detected.

Item 16

The method according to item 15, wherein the electrochemical device comprises two or more REs, two or more CEs, two or more WEs, wherein the electrodes are arranged as two or more three-electrode cell sensors, wherein each three-electrode cell sensor has a RE, CE, and WE.

Item 17

The method according to any of items 13-16, wherein the quorum sensing molecule is selected from the group consisting of: AHL, pyocyanin, PQS, and HHX.

Item 18 The method according to any of items 13-16, wherein the provided array of sensors is the array according to any of items 2-12.

Item 19

The method according to any of items 13-18, wherein the voltammetry is selected from the group consisting of: linear sweep voltammetry, staircase voltammetry, square wave voltammetry, differential pulse voltammetry and cyclic voltammetry, and more preferably is cyclic voltammetry and square wave voltammetry.

REFERENCES

[1] US 2009/0215079 A1
[2] WO 2014/015333 A1
[3] US 2008/0249391 A1

The invention claimed is:

1. An electrochemical device, comprising:
at least one reference electrode (RE);
at least one counter electrode (CE);
two or more working electrodes (WEs) for detecting a predetermined molecule;
wherein each working electrode differs from the other working electrode(s) with respect to at least one of the following characteristics: surface area, size, material, and coating;
a sample receiving area for receiving a biological sample,
wherein the working electrodes and the sample receiving area are fluidly connected such that each working electrode is in contact with the biological sample;
a display for displaying a result of the measurement;
the device configured for measuring the predetermined molecule within the biological sample;
the device configured for implementing a logic operable to determine a response for each working electrode, the response being a positive response or a negative response based on a comparison between voltammetry performed at the working electrode and a calibration value wherein a positive response is given when the peak value, correlatable to the predetermined molecule, matches the calibration value;
the display displaying a positive measurement if the response determined for each of the working electrodes is positive and not displaying a positive measurement if the response determined for any of the working electrodes is not positive.

2. The device according to claim 1, wherein the sample receiving area is configured to biological samples or body fluids selected from the group consisting of: blood, saliva, urine, sputum, dissolved tissue, and bronchoalveolar liquids.

3. The device according to claim 1, wherein the working electrodes and the sample receiving area are fluidly connected by a capillary network.

4. The electrochemical device according to claim 1, wherein:
the at least one reference electrode comprises two or more reference electrodes (REs);
the at least one counter electrode comprises two or more counter electrodes (CEs);

the electrodes being arranged as two or more three-electrode cell sensors, wherein each three-electrode cell sensor has a RE, CE, and WE, thereby forming an array of two or more three-electrode cell sensors.

5. The device according to claim 4, comprising an array of three, four, five or six sensors.

6. The device according to claim 4, comprising an array of four, five or six sensors.

7. The device according to claim 4, wherein the reference electrode material of one or more of the sensors is selected from the group consisting of: silver (Ag), silver chloride (AgCl), and platinum (Pt).

8. The device according to claim 4, wherein the reference electrode material of one or more of the sensors is silver (Ag).

9. The device according to claim 4, wherein the counter electrode of each sensor is identical to the working electrode of said sensor.

10. The device according to claim 4, wherein the working electrode material of one or more sensors is selected from the group consisting of: gold (Au), silver (Ag), platinum (Pt), ITO, P-dot, carbon, multiwalled carbon nanotubes, singlewalled carbon nanotubes, carbon nanofibers, graphene, carbon-platinum composites, multiwalled carbon nanotubes with gold nanoparticles, and any combination thereof.

11. The device according to claim 4, further comprising a sensor with a working electrode of carbon.

12. The device according to claim 4,
wherein the working electrode of one or more of the sensors has a diameter between 0.1-10 mm; and/or
comprising an array of three sensors, wherein the first sensor has a working electrode of gold with a first diameter, the second sensor has a working electrode of gold with a second diameter, and the third sensor has a working electrode of platinum.

13. The device according to claim 4, wherein the working electrode of one or more of the sensors has a diameter between 1-5 mm.

14. An electrochemical device, comprising:
at least one reference electrode (RE);
at least one counter electrode (CE);
two or more working electrodes (WEs) for detecting a predetermined molecule;
wherein each working electrode differs from the other working electrode(s) with respect to at least one of the following characteristics: surface area, size, material, and coating;
a sample receiving area for receiving a biological sample,
wherein the working electrodes and the sample receiving area are fluidly connected such that each working electrode is in contact with the biological sample;
a display for displaying a result of the measurement;
the device configured for measuring the predetermined molecule within the biological sample;
the device configured for implementing a logic operable to determine a response for each working electrode, the response being a positive response denoted by 1 or a negative response denoted by 0 based on a comparison between voltammetry performed at the working electrode and a calibration value wherein a positive response is given when the peak value, correlatable to the predetermined molecule, matches the calibration value;
the logic further operable to add up the response of each of the working electrodes into a sum;
the logic further operable to determine the result of measurement as being positive or negative depending on comparison of the sum with a total number of the working electrodes wherein the result is positive if the sum is equal to the total number of the working electrodes.

15. A method for detecting the presence of a predetermined quorum sensing molecule in a biological sample, comprising the steps of:
providing an electrochemical device, comprising at least one reference electrode (RE), at least one counter electrode (CE), and two or more working electrodes for detecting the predetermined quorum sensing molecule,
wherein each working electrode differs from the other working electrode(s) with respect to at least one of the following characteristics: surface area, size, material, and coating;
providing the biological sample to the electrodes;
applying voltammetry to the electrodes;
determining a response for each working electrode, the response being a positive response or a negative response based on a comparison between the voltammetry performed at the working electrode and a calibration value wherein a positive response is given when the peak value, correlatable to the predetermined quorum sensing molecule, matches the calibration value; and
displaying a positive measurement if the response determined for each of the working electrodes is positive and not displaying a positive measurement if the response determined for any of the working electrodes is not positive;
whereby the presence of a predetermined quorum sensing molecule is detected.

16. The method according to claim 15, wherein the electrochemical device comprises two or more REs, two or more CEs, two or more WEs, wherein the electrodes are arranged as two or more three-electrode cell sensors, wherein each three-electrode cell sensor has a RE, CE, and WE.

17. The method according to claim 15,
wherein the quorum sensing molecule is selected from the group consisting of: AHL, pyocyanin, PQS, and HHX; and/or
wherein the voltammetry is selected from the group consisting of: linear sweep voltammetry, staircase voltammetry, square wave voltammetry, differential pulse voltammetry and cyclic voltammetry.

18. The method according to claim 15, wherein the electrochemical device is the electrochemical device of claim 4.

19. The method according to claim 15, further comprising a step of displaying a result of the measurement.

20. A method for measuring a level of a predetermined quorum sensing molecule in a biological sample, comprising the steps of:
providing the electrochemical device of claim 1, comprising at least one reference electrode (RE), at least one counter electrode (CE), and two or more working electrodes,
wherein each working electrode differs from the other working electrode(s) with respect to at least one of the following characteristics: surface area, size, material, and coating;
providing the biological sample to the electrodes;
applying voltammetry to the at least first WE;
applying chronoamperometry to the at least second WE;

detecting a signal from voltammetry correlatable to the predetermined quorum sensing molecule; and correlating the signal from chronoamperometry to a concentration;

whereby the level of the predetermined quorum sensing molecules is detected.

21. The method according to claim 20, wherein the electrochemical device comprises two or more REs, two or more CEs, two or more WEs, wherein the electrodes are arranged as two or more three-electrode cell sensors, wherein each three-electrode cell sensor has a RE, CE, and WE.

* * * * *